United States Patent [19]

Peters

[11] Patent Number: 4,753,638

[45] Date of Patent: Jun. 28, 1988

[54] MEDICAL SYRINGE

[75] Inventor: Joseph L. Peters, London, England

[73] Assignee: Clinical Product Development, Ltd., Kent, England

[21] Appl. No.: 1,642

[22] PCT Filed: Apr. 8, 1986

[86] PCT No.: PCT/GB86/00194

§ 371 Date: Feb. 11, 1987

§ 102(e) Date: Feb. 11, 1987

[87] PCT Pub. No.: WO86/05989

PCT Pub. Date: Oct. 23, 1986

[30] Foreign Application Priority Data

Apr. 11, 1985 [GB] United Kingdom ............... 8509301

[51] Int. Cl.⁴ .................................................. A61M 5/18
[52] U.S. Cl. .................................... 604/212; 604/216
[58] Field of Search ............... 604/212, 213, 214, 215, 604/216

[56] References Cited

U.S. PATENT DOCUMENTS 3,557,788 1/1971 Swartz ........................... 604/212

FOREIGN PATENT DOCUMENTS 2072017 9/1971 United Kingdom.

Primary Examiner—John D. Yasko
Attorney, Agent, or Firm—Mason, Fenwick & Lawrence

[57] ABSTRACT

A device for use in surgical procedures formed of a concertina cartridge (1) of a resilient material. The cartridge (1) has a nozzle (5), the throat of which is designed to receive by snap-click action, a projection (9) formed internally of the chamber (1), to hold the cartridge in a collapsed, but resiliently releasable, state as it is compressed to that state under concertina action. The device has applicability to surgical procedures such as blood collection, drug infusion, and balloon catheter inflation while eliminating the dangers of bacterial infection always present when performing such procedures using devices and systems of the prior art.

7 Claims, 2 Drawing Sheets

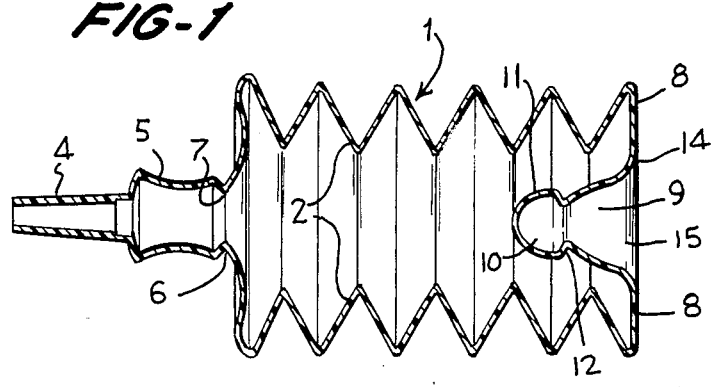
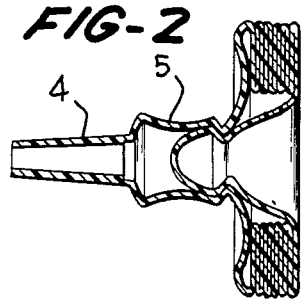
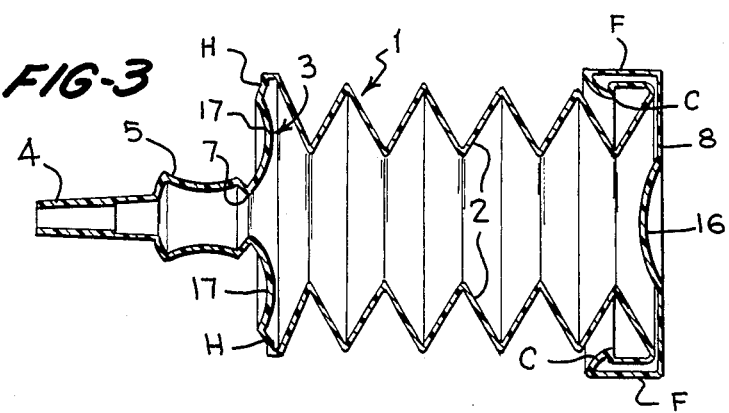
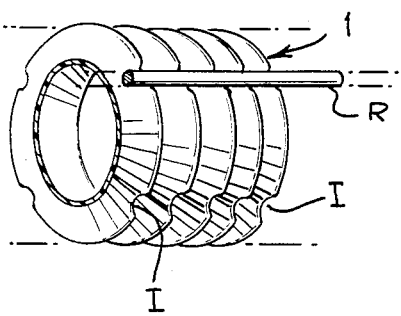

MEDICAL SYRINGE

FIELD OF THE INVENTION

The present invention relates to a device for use in surgical, medical and therapeutic procedures.

BACKGROUND ART

It is common practice for plastics or rubber tubes to be inserted into the tissues, cavities, orifices or veins of the human body.

Such tubes (otherwise known as catheters or cannulae) possess two channels down the central bore of the catheter. Whilst one (the larger) channel, is used for the infusion of fluid into or drainage out of the body, the other smaller diameter channel communicates with a latex balloon placed concentrically around the catheter shaft and close to the end of the tube which is left within a body cavity, e.g., the urinary bladder.

The other end of the smaller channel is protected by a plastic hub containing a displaceable rubber diaphragm which acts as a one-way valve. This secondary channel and valved-port permits the inflation of the balloon which then effectively engages upon the surrounding tissues of the body cavity and prevents the catheter from sliding out of the body.

The technique and procedure for inflating the balloon at the present time, involves a series of actions on the part of a nurse or doctor, including the manipulation and breaking open of an ampoule or bottle or sterile water or saline; the opening of a sterile packet containing an hypodermic type plastics syringe; the opening and use of a sterile needle or plastics quill from a packet to aspirate the contents of the ampoule into the syringe; and finally the insertion of the nozzle of the full hypodermic into the valved-inflation port of the catheter.

Moreover the resistance of the valve diaphragm must be overcome and a precise volume of fluid discharged into the balloon to achieve inflation, before the hypodermic syringe is removed from the inflation port.

It can be easily seen from the above that numerous components are required to perform the task and the risk of bacterial contamination during the various stages is an ever present potential problem.

Similarly, another common and important function of plastics tubes which have been partially inserted into the body is their use as a portal for access to the venous or arterial system.

In these circumstances, a short length of fine-calibre hollow plastics or rubber tubing is placed, by a variety of techniques, into the lumen or channel of a blood vessel through a small wound in the skin. The central channel of the hollow catheter thereby is able to conduct a variety of physiological fluids into the blood vascular system.

The ends of the cannulae external to the body surface are fitted with a plastics or metal female luer hub which conforms to an International Standard in respect of its internal configuration.

Into this female luer hub, can be fitted a male luer nozzle which also conforms to an International Standard specification.

The normal practice is for the male nozzle to be the end component of an infusion tubing system which slowly delivers fluid from an intravenous bottle or bag, under the influence of gravity or a mechanical roller-pump. At intervals, in the care of patients, the need for the infusion system can be dispensed with, in order to make the patients more mobile and allow them to walk freely about the wards and corridors.

To achieve this end, the female hub of the intravenous cannula is covered by a small plastics cap or plug. However, before this is performed, the cannula tubing must be filled with a saline solution (often containing an anticoagulant agent—heparin) to prevent coagulation of the blood within the cannula and adjacent blood vessels.

This procedure, as in the case of the catheter balloon inflation manoeuvre, also requires the same range of accessory equipment to be used as previously described in the preceding paragraphs, to accomplish the final objective.

SUMMARY OF THE INVENTION

It is an object of the invention to provide a device for use in surgical procedures which can simultaneously perform all the necessary functions required for the inflation of medical catheter balloons and the aseptic occlusion of the hubs of vascular cannulae and avoiding the problems and complexities as above described.

It is a further object of the invention to provide a device for use in surgical procedures such as drug infusion and blood collection which avoids the problems of bacterial infection and, in the case of blood collection, also the accidental injection of air into the patient.

According to the invention there is provided a device for use in surgical procedures comprising a cartridge, a nozzle on the cartridge adapted for connection to a medical catheter and/or tube, the walls of said cartridge being designed to allow the cartridge to be depressed by concertina action from an expanded state to a collapsed state to expel its contents through said nozzle, and means in the cartridge arranged to be interengageable with said nozzle as the cartridge moves to said collapsed state thereby to hold the cartridge in that state and close the nozzle.

With this device so defined it is possible simultaneously to inflate medical catheter balloons and occlude the hubs of vascular cannulae which previously required a variety of complicated procedures and accessory equipment not consonant with the achievement of the desired objective of avoidance of bacterial contamination and enhancement of efficiency and high standards of patient care.

It is also possible to employ the device to perform infusion of drugs, as a blood or body fluid collection device.

A good measure of the range of the objectives and advantages of the invention will be apparent from the following disclosure directed to more specific details of some examples whereby the invention may be put into practical effect.

BRIEF DESCRIPTION OF ACCOMPANYING DRAWINGS

Some embodiments of the invention will therefore be described hereinafter by way of example with reference to the accompanying drawings wherein;

FIG. 1 is a sectional view of a device for use in surgical procedures;

FIG. 2 shows the device of FIG. 1 moved from its expanded state as shown in that Figure, to a collapsed locked position;

FIG. 3 is a modified form of the device shown in FIG. 1;

FIG. 4 illustrates in perspective view, a further modification of the device for use in surgical procedures shown in either FIG. 1 or FIG. 3;

BEST MODES OF CARRYING OUT THE INVENTION

Figure 5:
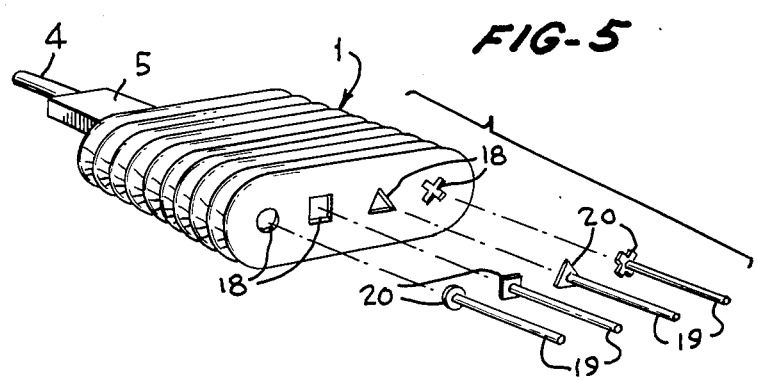
FIG. 5 is a perspective view of the device according to the invention modified for use in the administration of drugs.

The device for use in surgical procedures shown in the drawings comprises a main hollow cartridge chamber 1, the walls 2 of which are designed, either in circular, oval or rectangular cross-section, for concertina action between an expanded state, shown in FIGS. 1 and 3, and a collapsed state, as shown in FIG. 2.

The cartridge chamber 1 and its various component parts to be described, will normally be manufactured in a flexible plastics material using blow-mould technology to achieve the precise shapes required.

One end wall 3 of the cartridge chamber 1 has a centrally positioned integrally formed male luer cone shaped nozzle 4 which fits precisely current balloon inflation ports on medical catheters and vascular cannula female luer hubs (not shown).

The internal bore of the nozzle 4 has a depressed peripheral region 5 which forms a dilatation 6 near the throat of the nozzle 4 in conjunction with a constriction 7 between the dilatation 6 and the end wall 3 of the cartridge chamber 1.

Centrally positioned on the internal surface of the other end wall 8 of the cartridge chamber 1, is a projecting peg or stud 9 in axial alignment with the axis of the nozzle 4.

The stud 9 has a rounded head 10 the largest diametrial portion 11 of which is equal to the diameter of the dilatation 6 in the nozzle 4. The neck of the stud 9 tapers from a smallest diameter 12, equal to or less than the diameter of the constriction 7 in the nozzle 4, to a largest diameter 14 at its base 15 adjoining the end wall 8 of the cartridge chamber 1.

The outer surface of the end wall 8 of the cartridge chamber 1, see FIG. 3, is recessed at 16 conveniently to receive an operator's thumb. Similarly the outer surface of the end wall 3, each side of the nozzle 4, is recessed at 17 to accommodate the tips of two fingers of the operator, and by the combination of the recesses 16 and 17 the operator is able to apply a safe and controlled continuous pressure when using the device as will be explained.

Thus operated with one hand, the device acts as a small totally-closed pump, whereby pressure applied to the end wall 8 by the thumb towards the other end wall 3 controlled by the tips of two fingers of the same hand, expells the cartridge contents to be it air or liquid. Thus with liquid in the cartridge chamber 1 depression of the cartridge in the way described will cause the liquid to be ejected via the nozzle 4 through a medical catheter balloon inflation valve port or into an intravascular catheter.

Once the injection is completed in this way, the head 10 of the stud 9 will positively engage the throat of the nozzle 4 as by a snap-fit action as the portion 11 engages the dilatation 6 behind the constriction 7 with a pronounced click. The closing action will effectively prevent the reflux of any of the contained fluid or body fluid back into the chamber 1.

Due to the resiliency of the component parts of the device as described, release of the stud 9 from engagement with the throat of the nozzle 4 may be effected by simple finger pressure as will be appreciated.

This facility provides an effective hydraulic sealing cap for intravascular devices and prevents re-use and therefore bacterial contamination of the concertina cartridge. Because fluid contained in the chamber 1 is totally enclosed as it is ejected, the potential for bacterial contamination is also removed during this injection phase, in contrast to a conventional syringe barrel which has a small but definite space around the plunger allowing leakage, air entry and the entry of microorganisms.

In a modified form of the device, means may be provided, as shown in FIG. 3, to assist retention of the device in its collapsed state as shown in FIG. 1. This assistive means comprises the provision of resilient flanges F on the end wall 8 of the chamber 1 carrying catches C.

The other end wall 3 of the chamber 1 would then have complementary formations as at H to engage the catches C in the collapsed state.

A further modification of the device according to the invention not shown in the drawings may employ the use of a bayonet catch formed on the stud 9, the internal bore of nozzle 3 being suitably adapted to engage the bayonet catch in the collapsed state.

The device as described with reference to FIGS. 1 and 3 may be used as a syringe cartridge for the infusion of solutions of drugs of a wide variety of volumns at controlled rates by non-manual compression using non-mechanical or electrical infusion pumps.

In this application the precise flow rate of dispensed fluid is critical and therefore to prevent distortion of the concertina walls of the chamber 1, these walls may be provided with suitably positioned indents I as shown in the modification of FIG. 4, into which are located stiffening rods R which act as guide elements as the cartridge chamber is compressed.

In this application the syringe cartridge will be linked through the nozzle 4 by a short piece of flexible plastics tubing to a cannula or catheter (not shown) inserted into the body of a patient or animal.

By using such a system the need for complex plastics administration sets which rely upon gravity for the force of administration would be eliminated. This would be of particular value in patients requiring evacuation from accidents by air, sea or road transport. Current hypodermic syringes consist of a barrel and a separate plunger thus allowing the potential or bacterial entrance into the syringe chamber. It will be appreciated that the device of the invention avoids this hazard.

For multiple drug infusion applications each cartridge chamber, as shown in FIG. 5, may be provided with means 18, see FIG. 5, engageable with a drive shaft 19 of a mechanical or electrical infusion pump (not shown).

As shown at 18 in FIG. 5, the engagement means in a representative cartridge may take one of several forms, for example, square, circular, triangular or crossed shaped recesses.

In this case the drive shaft 19 shown in FIG. 5, of the infusion pump would be provided with end pieces 20 shaped for reception within the recesses 18 as appropriate.

Figure 6:
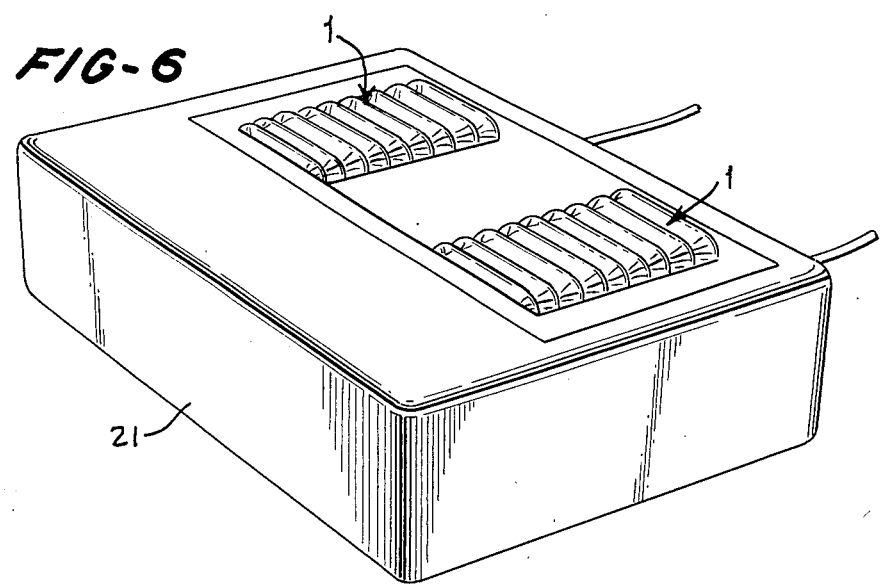
FIG. 6 illustrates how a bank of drug infusion devices may be assembled together for a multiple drug infusion procedure employing a syringe infusion pump.

The particular shaped recess in a representative drug infusion cartridge would then act as an identification of the drug in that cartridge so that a whole bank of cartridges 1 could be mounted to an appropriately designed and coded infusion pump, shown schematically as 21 in FIG. 6, and operated by micro-processor means (not shown) on a totally automatic, non-manual and precisely controlled basis.

The invention may also be used in another form as a blood or body fluid collection device. In this application the closure mechanism is illustrated in FIGS. 1, 2 and 3 allows the device to be delivered to the patients in a collapsed state and thus empty of any air. In this way the danger of accidental injection into the patient is avoided. For this application, the rearward end of the cartridge may be extended as a flange (not shown) for gripping between finger and thumb during the blood collection procedure.

In another form the device can be used to instill antiseptic solutions through the tap mechanisms of plastics urinary drainage collection bags. This effectively provides an antiseptic locking mechanism and prevents bacterial entry into the sterile urinary drainage system.

Other modifications will be readily apparent to one skilled in the art but such will fall within the scope of the inventions defined in the following claims.

I claim:

1. A device for use in surgical procedures comprising:
   a cartridge chamber having opposed end walls and a peripheral side wall;
   a nozzle extending from one of said end walls of said cartridge chamber adapted for connection to medical catheter means, said nozzle having a throat; and
   a shaped projection on the inside of said side wall of said cartridge chamber opposite said throat of said nozzle, said shaped projection having a peripheral recess;
   said peripheral side wall of said cartridge chamber having pleats to allow said cartridge chamber to be depressed by concertina action from an expanded state to a collapsed state to expel its contents through said nozzle; and
   said throat being resilient and having a constriction complimentary thereto in the throat of said nozzle for engaging said peripheral recess in said shaped projection when said cartridge chamber is in the collapsed state.

2. A device as claimed in claim 1 wherein said end wall of said cartridge chamber carrying said shaped projection is provided with exteriorly formed resilient projections which engage complimentary formations on the exterior of said other end wall of said cartridge chamber in the collapsed state of said cartridge chamber.

3. A device as claimed in claim 1, formed wholly of a resilient plastic material.

4. A device for use in surgical procedures comprising:
   a cartridge chamber having opposed end walls and a peripheral side wall;
   a nozzle extending from one of said end walls of said cartridge chamber adapted for connection to medical catheter means, said nozzle having a throat, said peripheral side wall of said cartridge chamber having pleats to allow said cartridge chamber to be depressed by concertina action from an expanded state to a collapsed state to expel its contents through said nozzle; and
   means in said cartridge chamber for arranging for interengaging with said nozzle as said cartridge chamber moves to said collapsed state thereby to hold said cartridge chamber in that state and close said nozzle, the outer edges of said pleats of said peripheral side wall being provided with indents carrying stiffening rods which form guide elements for said cartridge chamber during movement between the expanded and collapsed states.

5. A device as claimed in claim 4, formed wholly of a resilient plastic material.

6. A device for use in surgical procedures comprising:
   a cartridge chamber having opposed end walls and a peripheral side wall;
   a nozzle extending from one of said end walls of said cartridge chamber adapted for connection to medical catheter means, said nozzle having a throat, said peripheral side wall of said cartridge chamber having pleats to allow said cartridge chamber to be depressed by concertina action from an expanded state to a collapsed state to expel its contents through said nozzle;
   and means in said cartridge chamber arranged for interengaging with said nozzle as said cartridge chamber moves to said collapsed state thereby to hold said cartridge chamber in that state and close said nozzle;
   said end wall of said cartridge chamber opposite said nozzle being provided with a recess, said recess being shaped to receive a complimentary shaped end piece of the drive shaft of a syringe infusion pump to enable automatic controlled depression of said cartridge chamber thereby, and said recess being of variable cross-section from cartridge chamber to cartridge chamber, so providing identification means for a drug compound within said cartridge chamber.

7. A device for use in surgical procedures comprising:
   a cartridge chamber having opposed end walls and a peripheral side wall;
   a nozzle extending from one of said end walls of said cartridge chamber adapted for connection to medical catheter means, said nozzle having a throat, said peripheral side wall of said cartridge chamber having pleats to allow said cartridge chamber to be depressed by concertina action from an expanded state to a collapsed state to expel its contents through said nozzle; and
   means in said cartridge chamber arranged for interengaging with said nozzle as said cartridge chamber moves to said collapsed state thereby to hold said cartridge chamber in that state and close said nozzle;
   said end wall of said cartridge chamber opposite said nozzle being provided with a recess, said recess having a particular geometric shape representative of the identity of a particular drug and adapted to receive the complimentary shaped end piece of the drive shaft of a syringe infusion pump to enable automatic controlled depression of said cartridge chamber thereby.

* * * * *